US008431147B2

(12) United States Patent
Drapeau et al.

(10) Patent No.: US 8,431,147 B2
(45) Date of Patent: *Apr. 30, 2013

(54) MALLEABLE IMPLANTS CONTAINING DEMINERALIZED BONE MATRIX

(75) Inventors: Susan J Drapeau, Cordova, TN (US); Kathy L Remsen, Germantown, TN (US); William F McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 442 days.

This patent is subject to a terminal disclaimer.

(21) Appl. No.: 12/768,818

(22) Filed: Apr. 28, 2010

(65) Prior Publication Data

US 2010/0209474 A1 Aug. 19, 2010

Related U.S. Application Data

(63) Continuation of application No. 11/415,037, filed on May 1, 2006, now Pat. No. 7,838,022.

(51) Int. Cl.
*A61F 2/28* (2006.01)
*A61K 35/32* (2006.01)

(52) U.S. Cl.
USPC ........... 424/423; 424/488; 424/489; 424/549; 523/115

(58) Field of Classification Search ............ 424/423, 424/488, 489, 549; 523/115; 623/23.61
See application file for complete search history.

(56) References Cited

U.S. PATENT DOCUMENTS

| | | |
|---|---|---|
| 4,272,948 A | 6/1981 | Dolberg et al. |
| 4,394,370 A | 7/1983 | Jefferies |
| 4,430,760 A | 2/1984 | Smestad |
| 4,440,750 A | 4/1984 | Glowacki et al. |
| 4,472,840 A | 9/1984 | Jefferies |
| 4,485,097 A | 11/1984 | Bell |
| 4,789,663 A | 12/1988 | Wallace et al. |
| 4,863,732 A | 9/1989 | Nathan et al. |
| 5,124,273 A | 6/1992 | Minami |
| 5,162,114 A | 11/1992 | Kuberasampath et al. |
| 5,273,964 A | 12/1993 | Lemons |
| 5,275,954 A | 1/1994 | Wolfinbarger et al. |
| 5,284,655 A | 2/1994 | Bogdansky et al. |
| 5,290,558 A | 3/1994 | O'Leary et al. |
| 5,298,254 A | 3/1994 | Prewett et al. |
| 5,314,476 A | 5/1994 | Prewett et al. |
| 5,356,629 A | 10/1994 | Sander et al. |
| 5,405,390 A | 4/1995 | O'Leary et al. |
| 5,439,684 A | 8/1995 | Prewett et al. |
| 5,510,396 A | 4/1996 | Prewett et al. |
| 5,513,662 A | 5/1996 | Morse et al. |
| 5,516,532 A | 5/1996 | Atala et al. |
| 5,531,791 A | 7/1996 | Wolfinbarger, Jr. |
| 5,707,962 A | 1/1998 | Chen et al. |
| 5,711,957 A | 1/1998 | Patat et al. |
| 5,811,401 A | 9/1998 | Bucala et al. |
| 5,869,527 A | 2/1999 | Fang et al. |
| 5,948,426 A | 9/1999 | Jefferies |
| 5,972,385 A | 10/1999 | Liu et al. |
| 6,030,635 A | 2/2000 | Gertzman et al. |
| 6,117,979 A | 9/2000 | Hendriks et al. |
| 6,124,273 A | 9/2000 | Drohan et al. |
| 6,165,487 A | 12/2000 | Ashkar et al. |
| 6,180,606 B1 | 1/2001 | Chen et al. |
| 6,197,325 B1 | 3/2001 | MacPhee et al. |
| 6,200,606 B1 | 3/2001 | Peterson et al. |
| 6,214,368 B1 | 4/2001 | Lee et al. |
| 6,261,586 B1 | 7/2001 | McKay |
| 6,281,195 B1 | 8/2001 | Rueger et al. |
| 6,287,341 B1 | 9/2001 | Lee et al. |
| 6,293,970 B1 | 9/2001 | Wolfinbarger et al. |
| 6,294,041 B1 | 9/2001 | Boyce et al. |
| 6,294,187 B1 | 9/2001 | Boyce et al. |
| 6,297,213 B1 | 10/2001 | Oppermann et al. |
| 6,309,659 B1 | 10/2001 | Clokie |
| 6,311,690 B1 | 11/2001 | Jefferies |
| 6,326,018 B1 | 12/2001 | Gertzman et al. |
| 6,328,765 B1 | 12/2001 | Hardwick et al. |
| 6,331,312 B1 | 12/2001 | Lee et al. |
| 6,340,477 B1 | 1/2002 | Anderson |
| 6,346,515 B1 | 2/2002 | Pitaru et al. |
| 6,368,356 B1 | 4/2002 | Zhong et al. |
| 6,372,257 B1 | 4/2002 | Marchosky |
| 6,437,018 B1 | 8/2002 | Gertzman et al. |
| 6,444,252 B1 | 9/2002 | Gordon et al. |

(Continued)

FOREIGN PATENT DOCUMENTS

| | | |
|---|---|---|
| RU | 219797 C1 | 2/2003 |
| WO | WO0236147 A1 | 5/2002 |

(Continued)

OTHER PUBLICATIONS

Devore, D.P. et al., "Rapidly polymerized collagen gel as a smoothing agent in excimer laser photoablation," J. Refract. Surg., Jan.-Feb., 11(1):50-5.

Eskandari, M.M. etal. (2006). "In vitro re-mineralization of demineralized bone matrix in human serum." Clin Chem Lab Med. 2006;44(1):54-8.

Lee, Kenneth J.H. et al. (2005) "Demineralized bone matrix and spinal arthrodesis" The Spine Journal (5): 217S-223S.

Pacaccio, D. J., et al. (2005). Demineralized bone matrix: basic science and clinical applications. Clin Podiatr Med Surg North Am. Oct. 2005; 22(4): 599-606, vii.

Peitrzak, W.S., et al. (2005) "Demineralized bone matrix graft: a scientific and clinical case study assessment." J Foot Ankle Surq. Sep.-Oct. 2005;44(5):345-53.

(Continued)

*Primary Examiner* — Taeyoon Kim
(74) *Attorney, Agent, or Firm* — Sorell Lenna & Schmidt LLP (57) ABSTRACT

Described are malleable medical compositions such as pastes or putties that include solids combined with a liquid carrier. The solids include particulate collagen and particulate demineralized bone matrix. The liquid carrier includes an aqueous medium comprising a polysaccharide. Also described are methods for making and using such medical compositions.

15 Claims, 1 Drawing Sheet

U.S. PATENT DOCUMENTS

| | | | |
|---|---|---|---|
| 6,444,254 | B1 | 9/2002 | Chilkoti et al. |
| 6,458,375 | B1 | 10/2002 | Gertzman et al. |
| 6,576,015 | B2 | 6/2003 | Geistlich et al. |
| 6,576,016 | B1 | 6/2003 | Hochshuler et al. |
| 7,163,691 | B2 | 1/2007 | Knaack et al. |
| 2001/0014667 | A1 | 8/2001 | Chen et al. |
| 2001/0018614 | A1 | 8/2001 | Bianchi |
| 2001/0043940 | A1 | 11/2001 | Boyce et al. |
| 2002/0018796 | A1 | 2/2002 | Wironen et al. |
| 2002/0034531 | A1 | 3/2002 | Clokie |
| 2002/0071827 | A1 | 6/2002 | Petersen et al. |
| 2002/0072804 | A1 | 6/2002 | Donda |
| 2002/0076429 | A1 | 6/2002 | Wironen |
| 2002/0082697 | A1 | 6/2002 | Damien |
| 2002/0090725 | A1 | 7/2002 | Simpson et al. |
| 2002/0107570 | A1 | 8/2002 | Sybert et al. |
| 2002/0151985 | A1 | 10/2002 | Kuberasampath et al. |
| 2002/0197242 | A1 | 12/2002 | Gertzman et al. |
| 2003/0206937 | A1 | 11/2003 | Gertzman et al. |
| 2004/0097612 | A1 | 5/2004 | Rosenberg et al. |
| 2005/0020506 | A1 | 1/2005 | Drapeau et al. |
| 2007/0254041 | A1 | 11/2007 | Drapeau et al. |

FOREIGN PATENT DOCUMENTS

| | | | |
|---|---|---|---|
| WO | WO0208322 | A1 | 11/2002 |
| WO | WO03020327 | A2 | 3/2003 |
| WO | WO2005011764 | A1 | 2/2005 |

OTHER PUBLICATIONS

Lee, Yo-Po, et al. (2005). "The efficacy of difference commercially available demineralized bone matrix susbtances in an athymic rat model." J Spinal Disord Tech. 2005;18:439-444.

Ranly, Don M., DDS, et al. (2005). "Platelet-derived growth factor inhibits demineralized bone matrix-induced intramuscular cartilage and bone formation." The Journal of Bone of Joint Surgery, Inc., JBJS.orq, Sep. 2005; vol. 87-A, No. 9, 2052-64.

Ziran, B., et al. (2005). "Comparative efficacy of 2 different demineralized bone matrix allografts in treating long-bone nonunions in heavy tobacco smokers." Am J Orthop. Jul. 2005;34(7):329-32.

Han, Bo, et al. (2005). "Effect of moisture and temperature on the osteoinductivity of demineralized bone matrix." Journal of Orthopaedic Research, 23 (2005) 855-861.

Colnot, Celine, Ph.D, et al. (2005). "Mechanisms of action of demineralized bone matrix in the repair of cortical bone defects." Clinical Orthopaedics and Related Research, Jun. 2005, No. 435:69-78.

Bender, Sa, et al. (2005). "Evaluation of demineralized bone matrix paste and putty in periodontal intraosseous defects." J Periodontol. May 2005;76(5):768-77.

Schouten, C.C., et al. (2005) "DBM induced ectopic bone formation in the rat: The importance of surface area." Journal of Materials Science: Materials in Medicine, 16(2005)149-152.

Peterson, Brett, MD, etal. (2004). "Osteoinductivity of commercially available demineralized bone matrix." The Journal of Bone and Joint Surgery, Inc., JBJS.org, Oct. 2004; vol. 86-A, No. 10, 2243-50.

Bomback, David A., MD, et al. (2004). "Comparison of posterolateral lumbar fusion rates of grafton putty and OP-1 putty in an athymic rat model." Spine.2004, vol. 29, No. 15, 1612-1617.

Hartman, Ed H.M., MD, etal. (2004). "Demineralized bone matrix-induced ectopic bone formation in rats: In Vivo study with follow-up by Magnetic Resonance Imaging, Magnetic Resonance Angiography, and Dual-Energy X-Ray Absorptiometry." Tissue Engineering. vol. 10, No. 5/6, 2004, 747-754.

Traianedes, Kathy, et al. (2004). "Donor age and gender effects on osteoinductivity of demineralized bone matrix." J Biomed Mater Res B Appl Biomater. Jul. 15, 2004:70(1):21-9.

Klepp, M, et al. (2004). "Histologic evaluation of demineralized freeze-dried bone allografts in barrier membrane covered periodontal fenestration wounds and ectopic sites in dogs." J Clin Periodontol. Jul. 2004;3 1(7):534-44.

Louis-Ugbo, John, et al. (2004). "Evidence of Osteoinduction by Grafton Demineralized Bone Matrix in Nonhuman Primate Spinal Fusion." Spine, 2004, vol. 29, No. 4, 360-366.

Cammisa, Frank P., Jr., et al. (2004). "Two-Year Fusion Rate Equivalency Between Grafton DBM Gel and Autograft in Posterolateral Spine Fusion." Spine, vol. 29, No. 6, 660-666.

Blum, B, et al. (2004). "Measurement of bone morphogenetic proteins and other growth factors in demineralized bone matrix." Orthopedics. Jan. 2004;27(1Suppl):s161-5.

Etienne, G., et al. (2004). "Use of cancellous bone chips and demineralized bone matrix in the treatment of acetabular osteolysis: preliminary 2-year follow-up." Orthopedics. Jan. 2004;27(1 Suppl):s123-6.

Leatherman, DB, etal. (2004). "The use of demineralized bone matrix for mastoid cavity obliteration." Otol Neurotol. Jan. 2004;25(1):22-5; discussion 25-6.

Yee, Albert Juang Ming MD, et al. (2003). "Augmentation of Rabbit Posterolateral Spondylodesis Using a Novel Demineralized Bone Matrix-Hyaluronan Putty." Spine, vol. 28, No. 21, 2435-2440.

Stavropoulos A., et al. (2003). "Influence of demineralized bone matrix's embryonic origin on bone formation: an experimental study in rats." Clin Implant Dent Relat Res. 2003;5(3): 184-92.

Oaks, Daniel A., et al. (2003). "An Evaluation of Human Demineralized Bone Matrices in a Rat Femoral Defect Model." Clinical Orthopaedics and Related Research, No. 413, 281-290.

Han, Bo, et al. (2003). "Quantitative and sensitive in vitro assay for osteoinductive activity of demineralized bone matrix." Journal of Orthopaedic Research. 21 (2003)648-654.

Wilkins, RM, et al. (2003). "The effect of allomatrix injectable putty on the outcome of long bone applications." Orthopedics. May 2003;26(5Suppl):s565-70.

Turner, TM, et al. (2003). "Restoration of large bone defects using a hard-setting, injectable putty containing demineralized bone particles compared to cancellous autograft bone." Orthopedics. May 2003;26(5Suppl):s561-5.

Takikawa, Satoshi, et al. (2003). "Comparative evaluation of the osteoinductivity of two formulations of human demineralized bone matrix." J Biomed Mater Res A. Apr. 1, 2003;65(1):37-42. PM1D:12635152 [PubMed—indexed for Medline].

Cook, et al. (2002). "The effect of demineralized bone matrix gel on bone ingrowth and fixation of porous implants." J Arthroplasty. Jun. 2002;17(4):402-8. PMID: 12066267 [PubMed—indexed for Medline].

Dickman, Curtis A. (2001). Osteoinductive demineralized bone: what's the risk? Spine. Jul. 1, 2001;26(13):1409-10. No abstract available. PMID: 11458139 [PubMed—indexed for Medline].

Bostrom, MPG, et al. (2001). "An unexpected outcome during testing of commercially available demineralized bone graft materials." Spine, vol. 26, No. 13, 1425-1428.

Wang, Jeffrey C, et al. (2001). "Dose-Dependent toxicity of a commercially available demineralized bone matrix material." Spine, Jun. 1, 2001;26(13):1429-35;discussion 1435-6, PMID: 11458146 [PubMed—indexed for Medline].

Li H, et al. (2000), "Identification of bone morphogenetic proteins 2 and 4 in commercial demineralized freeze-dried bone allograft preparations: pilot study." Clin Implant Dent Relat Res. 2000;2(2):110-7. PMID: 11359264 [PubMed—indexed for Medline].

Maddox, Ewa, etal., (2000). "Optimizing human demineralized bone matrix for Clinical application." Tissue Eng. Aug. 2000:441-8. PMID: 10992439 [PubMed—indexed for Medline].

Russell, James L., (2002). "Grafton Demineralized Bone Matrix: Performance Consistency, Utility, and Value." Tissue Engineering, vol. 6, No. 4, 2000; 435-440.

Russell, JL, et al, (1999). "Clinical utility of demineralized bone matrix for osseous defects, arthrodesis, and reconstruction: impact of processing techniques and Study methodology." Orthopedics. May 1999;22(5):524-31; quiz 532-3. Review. PMID: 10348114 [PubMed—indexed for Medline].

Carnes, DL, et al., (1999). "Evaluation of 2 novel approaches for assessing the ability of demineralized freeze-dried bone allograft to induce new bone formation." J Periodontol. Apr. 1999;70(4):353-63. PMID: 10328645 [PubMed—indexed for Medline].

Hagino, T., et al., (1999). "Accelerating bone formation and earlier healing after using demineralized bone matrix for limb lengthening in rabbits." J Orthop Res. Mar. 1999; 17(2):232-7. PMID: 10221840 [PubMed—indexed for Medline].

Martin, George J., et al., (1999). "New formulations of demineralized bone matrix as a more effective graft alternative in experimental posterolateral lumbar spine arthrodesis." Spine. Apr. 1, 1999;24(7):637-45. PM1D:10209791 [PubMed—indexed for Medline].

Garraway R., et al., (1998). "An assessment of the osteoinductive potential of commercial demineralized freeze-dried bone in the murine thigh muscle implantation model." J Periodontol. Dec. 1998;69(12):1325-36. PMID9926762 [PubMed—indexed for Medline].

Edwards, JT., et al., (1998). "Osteoinduction of human demineralized bone:characterization in a rat model." ciin Orthop Reiat Res. Dec. 1998;(357):2i9-28. PMID:9917720 [PubMed—indexed for Medline].

Chesmel, KD, et al., (1998). "Healing response to various forms of human deminerlized bone matrix in athymic rat cranial defects." J Oral Maxiiofac Surg. Jul. 1998;56(7):857-63; discussion 864-5. PMID: 9663577 [PubMed—indexed for Medline].

Torricelli, P., etal., (1998). "In vitro osteoinduction of demineralized bone." Artif Cells Blood Substit Immobil Biotechnol. May 1998; 26(3):309-15. PMID:9635123 [PubMed—indexed for Medline].

Pinholt, EM, etal., (1998). "Osteoinductive potential of demineralized rat bone increases with increasing donor age from birth to adulthood." [PubMed—indexed for Medline] nor age from birth to adulthood. J Craniofac Surg. Mar. 1998;9(2): 142-6. PMID:9586543.

Morone, Michael A., et al., (1998). "Experimental Posterolateral Lumbar Spinal Fusion With a Demineralized Bone Matrix Gel." Spine. vol. 23(2), Jan. 15, 1998, 159-167.

Zhang, M et al., (1997). "Effect(s) of the demineralization process on the osteoinductivity of demineralized bone matrix." J Peridonontal. Nov. 1997;68(11):1085-92. PMID: 9407401 [PubMed—indexed for Medline].

Caplanis, N. et al., (1997). "Effect of allogeneic, freeze-dried, demineralized bone matrix on guided bone regeneration in supra-alveolar per-implant defects in dogs." Int J Oral Maxiilofac Implants. Sep.-Oct. 1997;12(5):634-42. PMID:9337024 [PubMed—indexed for Medline].

Becerra, J., et al. (1996). "Demineralized bone matrix mediates differentiation of bone marrow stromal cells in vitro: effect of age of cell donor." J Bone Miner Res. Nov. 1996;11 (11): 1703-14. PMID: 8915778 [PubMed—indexed for Medline].

Rabie, AB, et al., (1996). "The effect of demineralized bone matrix on the healing of intramembranous bone grafts in rabbit skull defects." J Dent Res. Apr. 1996;75(4):1045-51. PMID 8708134 [PubMed—indexed for Medline].

Nyssen-Behets C, et al., (1996). "Aging effect on inductive capacity of human demineralized bone matrix." Arch Orthop Trauma Surg. 1996;115(6):303-6. PMID:8905101 [PubMed—indexed for Medline].

Feighan, JE., et al., (1995). "Induction of bone by a demineralized bone matrix gel: a study in a rat femoral defect model." PMID:8544025 [PubMed—indexed for Medlinei.

Zhang, M. et al., (1997). "A quantitative assessment of osteoinductivity of human demineralized bone matrix." J Peridonontai. Nov. 1997;68(11):1076-84. PMID: 9407400 [PubMed—indexed for Medline].

Toba, Toshinari et al., "Regeneration of Canine Peroneal Nerve with the Use of a Polyglycolic Acid-Collagen Tube Filled with Laminin-Soaked Collagen Sponge: A Comparative Study of Collagen Sponge and Collagen Fibers as Filling Materials for Nerve Conduits," Japan Society for the Promotion of Science, Grant No. JSPS-RFTF 96100203 (2001).

Yarat, A. et al., "A method for preparing collagen graft materials," J. Marmara Univ. Dent. Fac, Sep. 1996; 2(2-3):527-9.

Ch, Tsai et al., "A composite graft material containing bone particles and collagen in osteoinduction in mouse," J. Biomed Mater Res., 2002:63(1 ):65-70.

Friess, W. et al., "Effects of processing conditions on the rheological behavior of collagen dispersions," Eur. J. Pharm. Biopharm, May 2001; 51(3):259-65.

Doillon, C.J. et al., "Collagen-based wound dressings: control of the pore structure and morphology," J Biomed Mater Res, Oct. 1986, 20(8): 1219-28.

Dung, S.Z. et al., "Degradation of insoluble bovine collagen and human dentine collagen pretreated in vitro with lactic acid, pH 4.0 and 5.5," Arch. Oral Biol., Oct. 1994, 39(10):901-5.

Devore, D.P. et al., "Rapidly polymerized collagen gel as a smoothing agent in excimer laser photoablation," J. Refract. Surg., Jan.-Feb., 11(1):50-5, 1995.

Kumar, A.J. etal., "Preoperative embolization of hypervascular head and neck neoplasms using microfibrillar collagen," AJNR Am. J. Neuroradiol., Mar.-Apr. 1982, 3(2):163-8.

Zhang, L. et al., "The modification of scaffold material in building artificial dermis," Artif. Cells Blood Substit. Immobil. Biotechnol.. Jul. 2002. 30(4):319-32.

Olde Damink, L.H. et al., "Cross-linking of dermal sheep collagen using a water-soluble carbodiimide," Biomaterials, Apr. 1996, 17(8):765-73.

Lee, J.D. et al., "Characterization of UV-irradiated dense/porous collagen membranes: morphology, enzymatic degradation, and mechanical properties," Yonsei Med. J., Apr. 2001, 42(2): 172-9.

Pietrucha, K., "Effect of irradiation on collagen solutions in relation to biomedical applications," Polim. Med., 1989, 19(1-2):3-18.

Kuijpers, A.J. et al., "In vivo compatibility and degradation of crosslinked gelatin gels incorporated in knitted Dacron," J Biomed Mater Res, Jul. 2000, 51(1):135-45.

Weadock, K.S. et al., "Effect of physical crosslinking methods on collagen-fiber durability in proteolytic solutions," J Biomed Mater Res, Oct. 1996, 32(2):221-6.

Roche, S. et al., "Native and DPPA cross-linked collagen sponges seeded with fetal bovine epiphyseal chondrocytes used for cartilage tissue engineering," Biomaterials, 2001, 22:9-18.

Schoof, Heike et al., "Control of Pore Structure and Size in Freeze-Dried Collagen Sponges," J Biomed Mater Res, 2001, 58:253-357.

Quteish, D. et al., "Development and testing of a human collagen graft material," J Biomed Mater Res, Jun. 1990, 24(6):749-60.

Curtil, A. et al., "Freeze drying of cardiac valves in preparation for cellular repopulation," Cryobiologv, Feb. 1997, 34(1): 13-22.

Wissink, M.J. et al., "Endothelial cell seeding on crosslinked collagen: effects of crosslinking on endothelial cell proliferation and functional parameters," Thromb. Haemost. Aug 2000, 84(2):325-31.

Pokharna, H.K. et al., "Collagen crosslinks in human lumbar intervertebral disc aging," Seine, Aug. 1998, 23(15):1645-8.

Zeeman, R., et al., "Crosslinking and modification of dermal sheep collagen using 1,4-butanediol diglvcidyl ether," J Biomed Mater Res, 1999, 46:424-33.

Gratzer, Paul F., et al., "Control of pH Alters the Type of Crosslinking Produced by 1-Ethyl-3-(3-Dimethylaminopropyl)-Carbodiimide (EDC) Treatment of Acellular Matrix Vascular Grafts," J Biomed Mater Res, 2001, 58:172-179.

Tachibana, Akira et al., "Fabrication of wool keratin sponge scaffolds for long-term cell cultivation," Journal of Biotechnology, 2002, 93:165-170.

Park, Si-Nae et al., "Characterization of porous collagen/hyaluronic acid scaffold modified by 1-theyl-3-(3-dimethylaminopropyl) carbodiimide crosslinking," Biomaterials, 2002, 23:1205-1212.

Billiar, Kristen et al., "Effects of carbodiimide crosslinking conditions on the physical properties of laminated intestinal submucosa," J Biomed Mater Res, 2001,56:101-108.

Zeeman, Raymond et al., "The kinetics of 1,4-butanediol diglycidyl ether crosslinking of dermal sheep collagen," J Biomed Mater Res, 2000, 51:541-548.

Zeeman, Raymond et al., "Successive epoxy and carbodiimide crosslinking of dermal sheep collagen," Biomaterials, 1999, 20:921-931.

Charulatha, V., et al., "Dimethyl 3,3'-dithiobispropionimidate: A novel crosslinking reagent for collagen," J. of Biomed. Mater Res., 2001, 54:122-128.

John, Annie et al., "A trial to prepare biodegradable collagen—hydroxyapatite composites for bone repair," J Biomater Sci Polymer Edn, 2001, vol. 12, No. 6, pp. 689-705.

Ueda, Hiroki et al., "Use of collagen sponge incorporating transforming growth factor-β1 to promote bone repair in skull defects in rabbits," Biomaterials, 2002, 23:1003-1010.

Sheu, Ming-Thau et al., "Characterization of collagen gel solutions and collagen matrices for cell culture," Biomaterials, 2001, 22:1713-1719.

Pieper, J.S. et al., "Development of tailor-made collagen-glycosaminoglycan matrices: EDC/NHS crosslinking, and ultrastructural aspects," Biomaterials, 2000, 21:518-593.

Doillon, C.J., et al., "Collagen-based wound dressings: Control of the pore structure and morphology," J. of Biomed. Mater Res., 1986, 20:1219-1228.

Wissink, M.J.B. et al., "Immobilization of heparin to EDC/NHS-crosslinked collagen. Characterization and in vitro evaluation," Biomaterials, 2001, 22:151-163.

Wissink, M.J.B. et al., "Binding and release of basic fibroblast growth factor from heparinized collagen matrices," Biomaterials, 2001, 22:2291-2299.

Van Wachem, P.B. et al., "In vivo biocompatibility of carbodiimide-crosslinked collagen matrices: Effects of crosslink density, heparin immobilization, and bFGF loading," J Biomed Mater Res, 2001, 55:368-378.

Taguchi, Tetsushi et al., "An improved method to prepare hyaluronic acid and type II collagen composite matrices," J Biomed Mater Res, 2002, 61:330-336.

Noah, Ernst Magnus et al., "Impact of sterilization on the porous design and cell behavior in collagen sponges prepared for tissue engineering," Biomaterials, 2002, 23:2855-2861.

Elbjeirami, Wafa M. et al., "Enhancing mechanical properties of tissue-engineered constructs via lysyl oxidase crosslinking activity," J Biomed Mater Res. 2003. 66A:513-521.

Schoof, Heike et al., "Control of Pore Structure and Size in Freeze-Dried Collagen Sponges." J Biomed Mater Res, 2001, 58:352-357.

Rocha, Lenaldo B., "Biocompatibility of anionic collagen matrix as scaffold for bone healing", Biomaterials, 2002, 23:449-456.

MALLEABLE IMPLANTS CONTAINING DEMINERALIZED BONE MATRIX

CROSS-REFERENCE TO RELATED APPLICATIONS

This application is a continuation of U.S. application Ser. No. 11/415,037, filed May 1, 2006, now U.S. Pat. No. 7,838,022, the entirety of which is incorporated by reference.

BACKGROUND

The present invention relates generally to medical implants. In more particular aspects, the present invention relates to osteoinductive implant formulations containing demineralized bone matrix.

A wide variety of implant formulations have been suggested in the art for the treatment of bone defects. In addition to traditional bone grafting, a number of synthetic bone graft substitutes have been used or explored, including some materials that contain demineralized bone matrix. Demineralized bone matrix has been shown to exhibit the ability to induce and/or conduct the formation of bone. It is thus desirable to implant and maintain demineralized bone matrix at a site at which bone growth is desired.

However, the beneficial nature of demineralized bone matrix is susceptible to disruption by the incorporation of incompatible materials or techniques when formulating the medical implant material. At the same time, effective implant compositions must exhibit properties that retain the demineralized bone matrix at the implant site, and that handle well in the operating environment. As well, it is of considerable commercial significance that the formulation be manufacturable without undue cost, equipment or material burdens.

In view of the background in the area of demineralized bone matrix formulations, there exist needs for product formulations which exhibit the ability to induce and/or support bone growth through a desired region, which are readily manufacturable, and which demonstrate acceptable handling properties for surgeons.

SUMMARY

In one aspect, the present invention provides a demineralized bone matrix composition. The composition comprises bioresorbable solids admixed with a liquid carrier to form a malleable implant composition, with the bioresorbable solids present at a level of about 0.1 grams per cubic centimeter (g/cc) to about 0.7 g/cc of the composition. The bioresorbable solids include a particulate solid collagen material and a particulate solid demineralized bone matrix material, with the particulate solid collagen material present in a weight ratio no less than about 1:12 and no greater than about 1:2 relative to the particulate solid demineralized bone matrix material. The liquid carrier comprises an aqueous gel including a biocompatible polysaccharide, with the biocompatible polysaccharide present at a level of about 0.01 g/cc to about 0.1 g/cc of the composition. The solid demineralized bone matrix material incorporated in the composition can exhibit osteoinductivity. In certain forms, such malleable compositions are flowable paste materials in which the bioresorbable solids are present at a level of about 0.1 g/cc to about 0.25 g/cc of the composition, and the polysaccharide is present at a level of about 0.01 g/cc to about 0.03 g/cc of the composition. In other inventive embodiments, such malleable compositions are shape-retaining putties in which the bioresorable solids are present at a level of about 0.2 g/cc to about 0.4 g/cc of the composition, and the polysaccharide is present at a level of about 0.02 g/cc to about 0.05 g/cc of the composition. The polysaccharide in these inventive compositions can be an alginate, pectin or chitosan material, with alginates providing particularly advantageous osteoinductive pastes and putties.

In another embodiment, the invention provides a demineralized bone matrix composition that contains a liquid carrier comprising an aqueous gel including a biocompatible polysaccharide, the aqueous gel in admixture with solids to form a malleable composition. The solids of this embodiment comprise a chemically crosslinked, particulate collagen material, and a particulate demineralized bone matrix material. The demineralized bone matrix composition can exhibit osteoinductivity.

In another embodiment, the invention provides a demineralized bone matrix composition that includes a liquid carrier comprising an aqueous gel including a biocompatible polysaccharide, the aqueous gel being in admixture with particulate solids to form a malleable composition. The particulate solids include a fragmented bioresorbable sponge material and a demineralized bone matrix material. The fragmented bioresorbable sponge material can comprise a sponge material that has been rendered to a particulate form, such as a randomly fragmented (e.g. milled) sponge material.

In further embodiments, the invention provides methods of making and methods of using malleable implant compositions as described herein, and medical products including such compositions or materials for making them packaged in a sterile condition.

Additional embodiments as well as features and advantages of the invention will be readily apparent to those of ordinary skill in the art from the descriptions herein.

DETAILED DESCRIPTION

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As disclosed above, in certain aspects, the present invention relates to implantable medical formulations, and to methods for making and using the formulations. In particular embodiments, the present invention provides medical formulations that include a malleable composition comprised of solids and a liquid carrier, such as paste or putty formulations. The solids include a substantial level of demineralized bone matrix particles. In particularly advantageous embodiments, the demineralized bone matrix particles will be effective to render the formulation osteoinductive when implanted in a mammalian patient, including a human patient. The liquid carrier advantageously includes an aqueous medium containing a polysaccharide, and especially a water soluble alginate.

Further, certain advantageous medical formulations include particulate collagen, such as collagen fibers or randomly fragmented collagen sponge, in an amount that is relatively less than the amount of particulate DBM on a dry weight basis. The inventive formulations desirably retain the DBM in a bioactive, osteoinductive condition, while also providing beneficial handling and implant properties.

Malleable implant formulations of the invention will include an amount of insoluble solids combined with the liquid carrier material. The solids include a particulate-form demineralized bone matrix material. In this regard, as used herein, the term "demineralized bone matrix" refers to a matrix material prepared by demineralizing any bone source, including cortical and/or cancellous bone. Desirable demineralized bone matrix materials will contain less than about 5% by weight of residual calcium. The source bone can be from any suitable source including autogenic, allogenic, and/or xenogenic bone. When used in describing a demineralized bone matrix (DBM) material, the term "osteoinductive" refers to the ability of the DBM material to induce bone growth. Alternatively, DBM materials can be provided lacking osteoinductive character, and nonetheless be used as osteoconductive materials that provide a scaffold capable of receiving bone growth induced by natural healing processes or other materials implanted in the patient.

DBM materials for use in the present invention can be obtained commercially or can be prepared by known techniques. In general, advantageous, osteoinductive DBM materials can be prepared by decalcification of cortical and/or cancellous bone, often by acid extraction. This process can be conducted so as to leave collagen, noncollagenous proteins, and growth factors together in a solid matrix. Methods for preparing such bioactive demineralized bone matrix are well known, in respect of which reference can be made to U.S. Pat. Nos. 5,073,373; 5,484,601; and 5,284,655, as examples. DBM products are also available commercially, including for instance, from sources such as Regeneration Technologies, Inc. (Alachua, Fla.), The American Red Cross (Arlington, Va.), and others. In certain embodiments, the particulate DBM material can have an average particle size of less than about 1,000 μm. For instance, the DBM material can have particle sizes in the range of 50 to 850 μm. DBM materials that are solely osteoconductive can be prepared using similar techniques that have been modified or supplemented to remove or inactivate (e.g. by crosslinking or otherwise denaturing) components in the bone matrix responsible for osteoinductivity. Osteoinductive and/or osteoconductive DBM materials used in the present invention can desirably be derived from human donor tissue, especially in regard to implant devices intended for use in human subjects.

Insoluble collagen material for use in the invention can be derived from natural tissue sources, e.g. xenogenic, allogenic, or autogenic relative to the recipient human or other patient) or recombinantly prepared. Collagens can be subclassified into several different types depending upon their amino acid sequence, carbohydrate content and the presence or absence of disulfide crosslinks. Types I and III collagen are two of the most common subtypes of collagen. Type I collagen is present in skin, tendon and bone, whereas Type III collagen is found primarily in skin. The collagen used in compositions of the invention can be obtained from skin, bone, tendon, or cartilage and purified by methods well known in the art and industry. Alternatively, the collagen can be purchased from commercial sources. Type I bovine collagen is preferred for use in the invention.

The collagen can be atelopeptide collagen and/or telopeptide collagen. Still further, either or both of non-fibrillar and fibrillar collagen can be used. Non-fibrillar collagen is collagen that has been solubilized and has not been reconstituted into its native fibrillar form.

Suitable collagen products are available commercially, including for example from Kensey Nash Corporation (Exton, Pa.), which manufactures a fibrous collagen known as Semed F, from bovine hides. Collagen materials derived from bovine hide are also manufactured by Integra Life Science Holding Corporation (Plainsboro, N.J.). Naturally-derived or recombinant human collagen materials are also suitable for use in the invention. Illustratively, recombinant human collagen products are available from Fibrogen, Inc. (San Francisco, Calif.).

The solid particulate collagen incorporated into the inventive compositions can be in the form of intact or reconstituted fibers, or randomly-shaped particles, for example. In certain beneficial embodiments, the solid particulate collagen will be in the form of particles derived from a sponge material, for example by randomly fragmenting the sponge material by milling, shredding or other similar operations. Such particulated sponge material can have an average maximum particle diameter of less than about 6 mm, more preferably less than about 3 mm, and advantageously in the range of about 0.5 mm to 2 mm. Such materials can, for example, be obtained by milling or grinding a porous sponge material and sieving the milled or ground material through a screen having openings sized about 6 mm or smaller, desirably about 0.5 mm to about 2 mm. Retch grinders with associated sieves are suitable for these purposes. The resulting small sponge particles are randomly formed and have generally irregular shapes with remnant structures from the sponge material, and are highly beneficial for use in malleable compositions such as pastes or putties of the invention. In this regard, the use of such particulated sponge materials in combination with DBM materials in malleable compositions is considered as an inventive aspect disclosed herein also wherein the sponge material is made all or in part from a bioresorbable material other than collagen. For example, the particulated sponge material can be made from any of the other natural or synthetic polymers disclosed herein. Likewise, in these particulated sponge embodiments, the liquid carrier can be a polysaccharide-containing substance as disclosed herein or another suitable material, including aqueous and non-aqueous liquid mediums, and the particulated sponge material can optionally be used in the same relative amounts disclosed herein for the collagen solids materials. Further, a sponge starting material has been chemically crosslinked with an aldehyde crosslinker such as formaldehyde or glutaraldehyde, or another suitable chemical crosslinker such as a carbodiimide, or by other techniques such as dehydrothermal or radiation-induced crosslinking, the particulated collagen or other bioresorbable material retains the chemical crosslinking and provides an advantageous, lasting scaffold for bone ingrowth. Other sources of chemically crosslinked, particulate collagen, in fiber, irregular or other shapes, can also be used to significant advantage, and their use is considered to be another aspect of the present invention. These crosslinked particulate materials can be provided as starting materials for preparing compositions as disclosed herein, and therefore as incorporated in the device these particles are individually crosslinked. As well, crosslinked solid collagen particles can be used in combination with non-crosslinked collagen in compositions of the invention, wherein the non-crosslinked collagen can be solid (insoluble) or soluble collagen, or combinations thereof. Such crosslinked and non-crosslinked collagen mixtures can be used, for example, to modulate the residence time of the collagen portion of the implant compositions in vivo.

Advantageous compositions of the invention can comprise bioresorbable solids at a level of about 0.1 grams per cubic centimeter (g/cc) to about 0.7 g/cc of the overall composition. For example, flowable paste compositions can be formulated which contain bioresorbable solids at a level of about 0.1 g/cc to about 0.25 g/cc, more typically in the range of about 0.15 g/cc to about 0.2 g/cc. Such flowable formulations can be configured as injectable materials, e.g. so as to be injectable through a needle that is 16 gauge or smaller. Certain shape-retaining putty compositions can be formulated which contain bioresorbable solids at a level of about 0.2 g/cc to about 0.5 g/cc, more typically in the range of about 0.25 g/cc to about 0.35 g/cc.

As noted above, malleable formulations of the invention include an amount of collagen as an insoluble solids material. The collagen will desirably be incorporated in a substantial, scaffold-providing amount, but in an amount less than that of the particulate DBM on a weight-to-weight basis. In certain compositional embodiments of the invention, the bioresorbable solids include the particulate solid collagen material and the DBM material at a collagen material:DBM material weight ratio (dry basis) of about 1:12 to about 1:2. More desirably, said weight ratio is in the range of about 1:12 to about 1:5, or about 1:10 to about 1:5. Particular inventive embodiments are provided wherein said weight ratio is in the range of about 1:8 to about 1:5. These malleable implant compositions thus include significant amounts of the collagen solids, which provide a local scaffold material for cellular infiltration and eventual new bone volume. Typically, the particles of such collagen solids are less dense than the DBM particles, which has not only been found to improved the physical handling and implant properties of the inventive materials but can also provide a local scaffold environment that is more susceptible to cellular infiltration than the DBM particles alone. These factors, combined with the biologically-friendly nature of a thickened polysaccharide carrier, provide osteoinductive materials of particular benefit to health care providers and patients.

The liquid combined with the solids of the inventive medical formulations can be an aqueous substance, and can comprise sterile water, physiological saline, phosphate buffered saline, blood-, bone marrow, bone marrow fractions or other liquid mediums, emulsions or suspensions that provide adequate wetting characteristics to form pastes, putties, and other similar malleable materials. Biocompatible organic liquids can be used in certain forms of the present invention, alone or in combination with water. A wide variety of biocompatible liquids are known and suitable for these purposes, including for instance liquid polyols such as glycerol.

The liquid phase of the medical implant compositions in accordance with certain aspects of the invention will comprise an amount of a polysaccharide. Preferred are ionic polysaccharides that are capable of forming thermally irreversible ionically-crosslinked gels upon combination with divalent or other polyvalent cationic materials. Suitable such polysaccharides include, as examples, plant-derived polysaccharides such as alginates and pectins, and gel-forming derivatives thereof. Aqueous solutions of such ionic polysaccharides form ionically-crosslinked gels upon contact with aqueous solutions of counter-ions. For instance, useful agents for ionically crosslinking alginate and pectin polysaccharides include cationic gelling agents, preferably including divalent or trivalent cations. Useful divalent cations for these purposes include the alkaline earth metals, especially calcium and strontium. Aluminum is a useful crosslinking trivalent cation. These ionic crosslinking agents will usually be provided by salts. Useful anionic counter-ions for the calcium or other salts are desirably selected from pharmaceutically-acceptable anions such as chlorides, gluconates, fluorides, citrates, phosphates, tartrates, sulphates, acetates, borates, and the like. An especially preferred ionic crosslinking agent for use with an alginate or pectin compound is provided by calcium chloride. The ionic polysaccharide chitosan can also be used, and can be ionically crosslinked with multivalent, anionic gelling agents. Such agents include metal polyphosphates, such as an alkali metal or ammonium polyphosphate, pyrophosphates or metaphosphates. Citrates can also be used. These anionic crosslinking agents will also usually be provided by salts. The cationic counter-ion for the polyphosphate or other salt can be any suitable, biocompatible or pharmaceutically-acceptable cation including for instance sodium, potassium, or ammonium. Many other biocompatible polysaccharides, including plant-derived and animal-derived materials, as well as corresponding ionic crosslinking agents, are known and can also be used in aspects of the present invention.

While the use of those ionic polysaccharides that are capable of forming thermally-irreversible ionically-crosslinked gels is preferred, it will be understood that in the present invention these polysaccharides will be ionically crosslinked, if at all, only to an extent that does not eliminate the malleable nature of the putty, paste or other similar implant material of the present invention. Thus, within aspects of the present invention, no or substantially no ionic crosslinking agent will be added, or in some cases only a relatively small amount of gelling can be added in order to increase the viscosity of the overall formulation. On the other hand, in other aspects of the invention, malleable compositions as described herein can be contacted with an amount of a liquid medium containing an ionic crosslinking agent immediately prior to, during, or after implantation of the material into a patient. Illustratively, a malleable composition as described herein can be co-administered with a liquid medium of ionic crosslinker, as in the case of a dual-barrel syringe administration by which the malleable composition and crosslinker are admixed as they exit the syringe. Alternatively, a previously-implanted amount of the malleable composition can be washed with a solution or other liquid medium containing an appropriate ionic crosslinking agent to stiffen the implanted material in situ.

The polysaccharide will typically be incorporated into malleable formulations of the invention at a relatively low level. Accordingly, in certain inventive variants, the malleable implant compositions of the invention contain the polysaccharide at a level of about 0.01 g/cc to about 0.1 g/cc of the overall composition, more typically at a level of about 0.01 g/cc to about 0.07 g/cc. In desirable flowable paste formulations, the overall composition can contain the polysaccharide at a level of about 0.01 g/cc to about 0.03 g/cc, more preferably about 0.015 to about 0.025 g/cc. In certain desirable shape-retaining putty formulations, the overall composition can contain the polysaccharide at a level of about 0.02 g/cc to about 0.07 g/cc, more typically about 0.02 g/cc to about 0.05 g/cc, and most desirably about 0.02 g/cc to about 0.04 g/cc.

Figure 1:
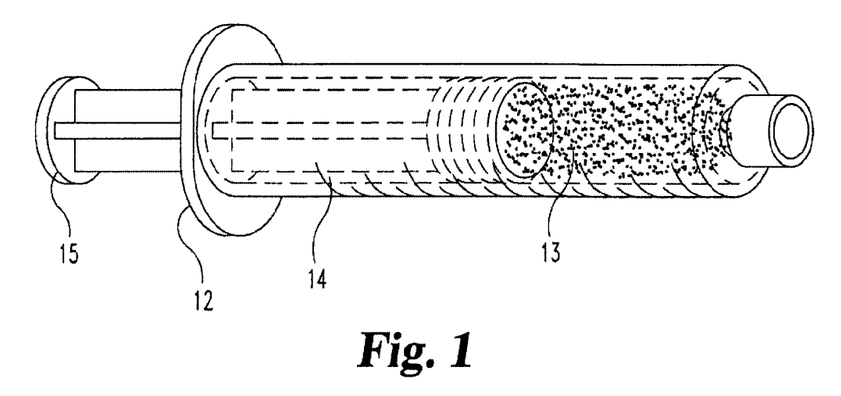
FIG. 1 provides a perspective view of a medical product of the invention including a medical paste or putty of the invention packaged within a terminally sterilized syringe device.

Compositions of the present invention can be manufactured in a ready-to-use format and packaged in a medically acceptable container for wetted malleable materials. In some embodiments, as illustrated in FIG. 1, the ready-to-use medical product can be a product 11 including a syringe device 12 containing an amount of a malleable composition 13 of the invention. The composition is contained within syringe barrel 14, and is transferable from the barrel 14 by actuating a plunger 15.

Figure 2:
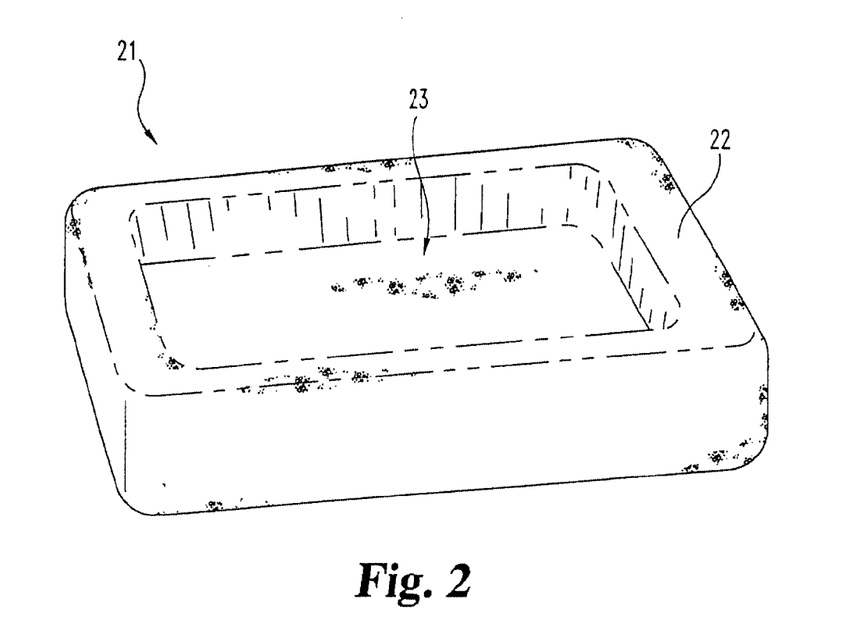
FIG. 2 provides a perspective view of a dry disruptable body that can be used to prepare malleable implant compositions of the invention.

Compositions of the invention can also be prepared on-site, at or near the time of surgery. For instance, dry materials can be provided in the appropriate amounts, and a suitable liquid such as a buffered aqueous solution can be combined with the dry materials and mixed to form malleable implant compositions. With reference to FIG. 2, in one form, an inventive product 21 includes a body 22 of dry materials including the DBM material, collagen material, and polysaccharide is provided. Body 22 can optionally define a reservoir 23 for receiving and retaining amounts of the liquid medium to be combined with the dry materials as it soaks into the body 22. The body 22 can thereafter be disrupted, e.g. by manual kneading, mixing or otherwise, to form the malleable composition.

In regard to the incorporated materials considered on a dry weight basis, the particulate DBM material can constitute about 40% to about 90% of the inventive compositions, more preferably about 50% to about 90%, and most preferably about 60% to about 85% by weight. In a similar vein, preferred inventive formulations can contain about 5% to about 30% by weight insoluble collagen particulate on a dry weight basis, more preferably about 8% to about 20%, and most preferably about 10% to about 15%; and can contain the polysaccharide at a level of about 1% to about 20% on a dry weight basis, more preferably about 5% to about 15%, and most preferably about 8% to about 12%. It will be understood, however, that other amounts of these materials can be used within the broader aspects of the present invention.

Further, when considered as a solvated component of the liquid phase of the composition (i.e. excluding the weight of the solids), the polysaccharide can for example be present as an about 1% to about 5% solution. Illustrative pastes can contain the polysaccharide in the liquid phase as an about 1 wt % to about 3 wt % solution, more preferably about 1.5 wt % to 2.5 wt %. Illustrative, shape-retaining putties can contain the polysaccharide in the liquid phase as an about 3 wt % to 5 wt % solution, more preferably about 3.5 wt % to 4.5 wt %.

In desirable variants, the liquid carrier of the inventive compositions is essentially or completely free from any organic compound that is a liquid at ambient or use (e.g. about 37° C.) temperatures. Thus, the use of organic solvents can be avoided, and the liquid carrier in certain forms can consist or consist essentially of an aqueous solution (potentially buffered) of one or more polysaccharides that is/are effective to provide the desired consistency to the final formulation. With respect to the admixed solids, these can be at least largely made up (e.g. at least about 60%, at least about 80%, or at least about 90% by weight) by the solid collagen particles and the solid DBM particles, and in certain embodiments the insoluble solids in the composition can consist or consist essentially of the collagen particles and DBM particles. As well, in desirable embodiments of the invention, all of the solids in the composition will be bioresorbable. It will be understood, however, that these parameters are not necessary to all aspects of the invention.

Certain advantageous malleable compositions of the invention will contain a particulate DBM material at a level of at least about 5% by weight overall, and typically within the range of about 5% to about 30%. Such compositions can contain the particulate solid collagen material at a level of at least about 0.5% by weight overall and typically in the range of about 0.5% by weight to about 5%, and the polysaccharide at a level of at least about 0.1% by weight overall and typically in the range of about 0.5% to 5%. More specific inventive malleable compositions incorporate the particulate DBM material at a level of about 10% to about 25% by weight overall, the particulate solid collagen material at a level of about 1% to about 5% by weight overall, and the polysaccharide at a level of about 1% to about 5% by weight overall.

The bulk densities of the inventive compositions can vary and depend upon the densities of the materials in the compositions. In certain embodiments, the bulk density of the inventive malleable composition will be in the range of about 1.1 g/cc to about 1.5 g/cc, more typically in the range of about 1.1 g/cc to about 1.4 g/cc. These densities may vary, however, with the densities of additional materials incorporated into the malleable compositions. For instance, bulk densities within these ranges or higher may be exhibited when amounts of dense solids such as particulate mineralized bone or ceramics are incorporated into the formulations.

Malleable implant materials of the invention may also contain other beneficial substances including for example preservatives, cosolvents, suspending agents, viscosity enhancing agents, ionic strength and osmolality adjusters and/or other excipients. Suitable buffering agents can also be used an include but are not limited to alkaline earth metal carbonates, phosphates, bicarbonates, citrates, borates, acetates, succinates, or others. Illustrative-specific buffering agents include for instance sodium phosphate, sodium citrate, sodium borate, sodium acetate, sodium bicarbonate, sodium carbonate, and sodium tromethanine (TRIS). These agents can be included in amounts that are effective to maintain the pH of the system at a biologically acceptable level, for instance maintaining a pH between about 6 and about 8 and preferably near neutral.

The malleable implant materials disclosed herein can also include other biocompatible and preferably bioresorbable substances. These materials may include, for example, natural polymers such as proteins and polypeptides, glycosaminoglycans, proteoglycans, elastin, hyaluronic acid, dermatan sulfate, or mixtures or composites thereof. Synthetic polymers may also be incorporated into the malleable implant materials. These include, for example biodegradable synthetic polymers such as polylactic acid, polyglycolide, polylactic polyglycolic acid copolymers ("PLGA"), polycaprolactone ("PCL"), poly(dioxanone), poly(trimethylene carbonate) copolymers, polyglyconate, poly(propylene fumarate), poly(ethylene terephthalate), poly(butylene terephthalate), polyethyleneglycol, polycaprolactone copolymers, polyhydroxybutyrate, polyhydroxyvalerate, tyrosine-derived polycarbonates and any random or (multi-) block copolymers, such as bipolymer, terpolymer, quaterpolymer, etc., that can be polymerized from the monomers related to previously-listed homo- and copolymers.

The malleable implant materials of the invention can also include a mineral component. The mineral used can include a natural or synthetic mineral that is effective to provide a scaffold for bone ingrowth. Illustratively, the mineral matrix may be selected from one or more materials from the group consisting of bone particles, Bioglass®, tricalcium phosphate, biphasic calcium phosphate, hydroxyapatite, corraline hydroxyapatite, and biocompatible ceramics. Biphasic calcium phosphate is a particularly desirable synthetic ceramic for use in the invention. Such biphasic calcium phosphate can have a tricalcium phosphate:hydroxyapatite weight ratio of about 50:50 to about 95:5, more preferably about 70:30 to about 95:5, even more preferably about 80:20 to about 90:10, and most preferably about 85:15. The mineral material can be a granular particulate having an average particle diameter between about 0.2 and 5.0 mm, more typically between about 0.4 and 3.0 mm, and desirably between about 0.4 and 2.0 mm.

In another aspect of the invention, the mineral material can include bone particles, possibly cancellous but preferably cortical, ground to provide an average particle diameter among those discussed above for the particulate mineral material. Both human and non-human sources of bone are suitable for use in the instant invention, and the bone may be autographic, allographic or xenographic in nature relative to the mammal to receive the implant. Appropriate pre-treatments known in the art may be used to minimize the risks of disease transmission and/or immunogenic reaction when using bone particles as or in the mineral material.

In one embodiment, xenogenic bone that has been pre-treated to reduce or remove its immunogenicity is used to provide a porous mineral matrix in the implant composition. For example, the bone can be calcined or deproteinized to reduce the risks of immunogenic reactions to the implant material.

Bioactive agents can be delivered with malleable implant materials of the invention. These bioactive agents may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholnergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenlcs, non-steroidal anti-inflammatory agents, steroidal anti-inflammatory agents, antioxidants, vaso-active agents, bone-active agents, osteogenic factors, antiarthritics, and diagnostic agents.

Bioactive agents may also be provided by tissue materials incorporated into the malleable implant material, including for instance autologous or allogenic tissue materials, which are incorporated into the material to be implanted in the patient. Such tissue materials can include blood or blood fractions, bone marrow or bone marrow fractions, and/or other sources of cells or-other beneficial tissue components derived from the patient to be treated or another suitable animal source.

Bioactive agents such as those described herein can be incorporated homogeneously or regionally into the implant material by simple admixture or otherwise. Further, they may be incorporated alone or in conjunction with another carrier form or medium such as microspheres or another microparticulate formulation. Suitable techniques for forming microparticles are well known in the art, and can be used to entrain or encapsulate bioactive agents, whereafter the microparticles can be dispersed within the malleable implantable material upon or after its preparation.

In certain embodiments, a malleable implant composition of the invention will include one or more substances, additional to the osteoinductive DBM material, that induce or generate the formation of bone. Suitable osteogenic materials can include a growth factor that is effective in inducing formation of bone. Desirably, the growth factor will be from a class of proteins known generally as bone morphogenic proteins (BMPs), and can in certain embodiments be recombinant human (rh) BMPs. These BMP proteins, which are known to have osteogenic, chondrogenic and other growth and differentiation activities, include rhBMP-2, rhBMP-3, rhBMP4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14.

For example, BMP-2, BMP-3, BMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in U.S. Pat. Nos. 5,965,403 and 6,331,612. Other compositions which may also be useful include Vgr-2, and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these patents and applications are hereby incorporated herein by reference. Also useful in the present invention are heterodimers of the above and modified proteins or partial deletion products thereof. These proteins can be used individually or in mixtures of two or more. rhBMP-2 is preferred.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-beta superfamily, such as activins, inhibins and TGF-beta 1 (e.g., a heterodimer composed of one monomer each of a BMP and a related member of the TGF-beta superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon several factors including the size and nature of the defect being treated, and the carrier and particular protein being employed.

Other therapeutic growth factors or substances may also be used in malleable implant materials of the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-α and TGF-β.

The osteogenic proteins or other biologically active agents, when used in the present invention, can be provided in liquid formulations, for example buffered aqueous formulations. In certain embodiments, such liquid formulations can be mixed with, received upon and/or within, or otherwise combined with a dried implant material containing solid ingredients in order to prepare an osteogenic, malleable implant material of the invention. One suitable rhBMP-2 formulation is available from Medtronic Sofamor Danek, Memphis, Tenn., with its INFUSE® Bone Graft product. Alternatively, such liquid formulations of biologically active agents can be combined with an already-prepared, wetted malleable implant composition of the invention.

Osteoinductive medical paste, putty or other malleable compositions of the present invention can also comprise progenitor and/or stem cells derived from embryonic or adult tissue sources and/or taken from culture. Illustratively, compositions of the invention can incorporate cells derived from blood, bone marrow, or other tissue sources from the patient to be treated (autologous cells) or from a suitable allogenic or xenogenic donor source. In certain embodiments of the invention, the conformable compositions incorporate an enriched bone marrow fraction, prepared for example as described in US Patent Publication No. 2005/0130301 to McKay et al. published Jun. 16, 2005, publishing U.S. patent application Ser. No. 10/887,275 filed Jul. 8, 2004, which is hereby incorporated herein by reference in its entirety. Thus, implantable materials can incorporate a bone marrow fraction enriched in connective tissue growth components, that is prepared by centrifuging a biological sample (e.g. from the patient to be treated) to separate the sample into fractions including a fraction rich in connective tissue growth components. The fraction rich in connective tissue growth components can then be isolated from the separated sample, and incorporated into the malleable implant material, e.g. by using the fraction in or as a wetting medium in combination with a dry particulate or dried body including the other ingredients of the malleable formulation.

In still further embodiments, the present invention provides methods for treating patients that involve implanting in the patients a malleable implant material as described herein. In such uses, a paste, putty or other malleable implant composition of the invention can be implanted at a site at which tissue growth is desired, e.g. to treat a disease, defect or location of trauma, and/or in some instances to promote artificial arthrodesis. The medical compositions can be used as or in surgical implants at, in, on, or near bone defect sites, cartilage repair sites, or other musculoskeletal sites. Alternatively, the compositions of the invention may be applied to larger segments of bone, artificial implants, or any other kind of surgical implant. The malleable character of the compositions can enable their introduction, shaping and/or molding within voids, defects or other areas in which new tissue growth is desired, and/or in certain embodiments in which the delivery of a bioactive agent is desired. In some advantageous embodiments, the malleable material will be a putty having shape-retaining properties that desirably provide sufficient three-dimensional integrity to resist substantial compression when impinged by adjacent soft tissues of the body at a bony implant site. In other advantageous embodiments, the malleable material will be a more flowable paste, thereby facilitating its introduction into remote implant sites using syringes, needles, tubes or other elongate delivery devices. Injectable pastes, for instance effective for injection through a 16 gauge needle, form preferred past embodiments of the invention.

Illustrative bone repair sites that can be treated with medical compositions of the invention include, for instance, those resulting from injury, defects brought about during the course of surgery, infection, malignancy or developmental malformation. The malleable compositions can be used in a wide variety of orthopedic, periodontal, neurosurgical and oral and maxillofacial surgical procedures including, but not limited to: the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the malleable composition or an implant comprising the composition include, but are not limited to: the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

In accordance with certain aspects of the invention, the paste, putty or other malleable implant compositions of the invention can be used as bone void fillers, or can be incorporated in, on or around a load bearing implants such as spinal implants, hip implants (e.g. in or around implant stems and/or behind acetabular cups), knee implants (e.g. in or around stems). In inventive variants, the malleable implant compositions of the invention can be incorporated in, on or around a load-bearing spinal implant device having a compressive strength of at least about 10000 N, such as a fusion cage, dowel, or other device potentially having a pocket, chamber or other cavity for containing an osteoinductive composition, and used in a spinal fusion such as an interbody fusion. One illustrative such use is in conjunction with a load-bearing interbody spinal spacer to achieve interbody fusion. In these applications, the malleable implant composition can be placed in and/or around the spacer to facilitate the fusion.

Illustrative cartilage repair sites that can be treated with malleable compositions of the invention include, as examples, articular cartilage surfaces occurring in articular joints having at least two major bones. Examples include, but are not limited to the elbow, wrist, phalanx, knee, and ankle. Additionally, cartilage surfaces within shoulder and hip joints can be treated.

The present invention also provides medical kits that include, or that can be used to prepare, malleable implant compositions of the invention. Such kits can include a dried material containing the solid ingredients of the malleable formulation along with an aqueous medium or other biocompatible wetting liquid for combination with the dried material to form a malleable wetted material, or can include the formulated, wetted malleable implant material in a suitable container such as a syringe or vial (e.g. terminally sterilized), and/or another item such as a load-bearing implant (e.g. a spinal spacer), and/or a transfer device such as a syringe, and/or a therapeutic substance, for example an osteogenic substance such as a BMP. In one specific form, such a medical kit can include a dried material, such as a particulate or dried body, a BMP in lyophilized form (e.g. rhBMP-2), and an aqueous medium for reconstitution of the BMP to prepare an aqueous formulation that can then be added to the dried material in the process of preparing an osteogenic putty, paste or other malleable implant material of the invention.

The invention will now be more particularly described with reference to the following specific examples. It will be understood that these examples are illustrative and not limiting of the embodiments of the invention.

Example 1

Preparation of Osteoinductive Putty Formulation 12.9 g of sodium alginate (USP grade, Spectrum Chemical) were combined with 325 cc of phosphate buffered saline in a blender. The materials were mixed in the blender until all of the alginate was incorporated. The combined PBS/alginate material was then transferred to a mixer bowl and mixing was initiated. 16.13 g of milled, crosslinked collagen sponge were slowly added to the mixer bowl while mixing, and the resulting materials mixed to form a uniform mixture. The milled collagen was obtained by grinding a crosslinked collagen sponge material available from Collagen Matrix, Inc. (Franklin Lakes, N.J.) and known as Collagen Matrix Sponge. A retch grinder operating at 8000 rpm with a 1 mm sieve was used for this purpose, resulting in the collection of the randomized sponge particulate as a wispy mass. 100 g of demineralized bone matrix having a particle size of 55-850 μm were then slowly added to the bowl while mixing, which was allowed to proceed until a uniform mixture was obtained. The resulting mass of putty was packed into a 60 cc syringe, and a syringe connector was attached. The 60 cc syringe was connected in sequence to smaller syringes for final packaging. In particular, 5 cc of the putty product were transferred into 6 cc syringes, and/or 10 cc of the putty product were transferred into 12 cc syringes. The top of the smaller syringe was then capped tightly, and the capped syringe was inserted into an inner pouch package which was vacuum sealed. Appropriate labels were applied to the inner pouches which were then inserted into outer packaging pouches and then heat sealed. The packaged syringe products were terminally sterilized with E-beam to a level of 25 kiloGrays (kGy).

The osteoinductive putties prepared as above contained, on a dry weight basis, 77.5% DBM (particle size 55-850 μm), 10.0% alginate, and 12.5% collagen. On a wet weight basis, the putties contained 21.4% DBM, 2.8% sodium alginate, 3.4% collagen, and 72.4% phosphate buffered saline. The compositions were of good putty quality and would retain their shape unless kneaded or pressed upon.

Example 2

Preparation of Osteoinductive Paste Formulation

The procedures of Example 1 were repeated except utilizing 660 cc of phosphate buffered saline instead of 325 cc. The resulting products were of a paste character and on a dry weight basis contained the same levels of DBM, sodium alginate, and collagen as the putties prepared in Example 1. On a wet weight basis, the paste contained 12.7% DBM, 1.6% sodium alginate, 2.0% collagen, and 83.7% phosphate buffered saline. The composition had a beneficial paste consistency and was manually injectable through a 16 gauge needle.

Example 3

Spinal Fusion Study with Osteoinductive Pastes and Putties

In this study, the osteoinductive paste and putty materials of Examples 1 and 2 were evaluated for their ability to induce spinal vertebral fusion when bilaterally implanted in the nude rat model.

Athymic nude rats (RNU/RNU) ranging in weight from 212-3000 grams were obtained from Harlan Laboratories. Test rats were divided into groups comprised of 6 animals according to weight. Control animals received sham surgery (no test implant).

For anesthesia, animals were placed in a chamber and induced with isoflurane in oxygen (2-4%). Buprenorphine (0.5 mg/kg) was administered pre-operatively for analgesia, and 0.2 ml enrofloxacin was administered subcutaneously for antimicrobial prophylaxis prior to surgery.

A dorsal midline skin incision was made from the region of L1-2 extending caudal approximately 3-4 cm to just caudal to the ileac crests. Paramedian incisions of approximately 2 cm were made over the paraspinal fascia, and muscles were separated with a combination of blunt and sharp dissection. Self-retaining retractors were placed to retract the muscle to expose the transverse vertebral processes. The transverse processes of the 4th and 5th lumbar vertebrae were identified and adherent soft tissue cleaned from the dorsal surfaces. The operative sites were both flushed with approximately 1.5 ml saline. A small, motorized burr was then used to decorticate the transverse processes to the point that bleeding bone was observed. The paste or putty was then applied to the sites. 0.3 ml of paste or putty compositions were applied to each site in direct contact with the decorticated transverse processes and spanned the distance between them.

Surgical closure was performed in two layers using monofilament polyglyconate suture (4-0 Maxon, Tyco Healthcare). After closure, a povidone iodine ointment was placed on the wound, followed by application of a Tegaderm (3M Healthcare) transparent dressing. A dorso-ventral radiograph was taken, and animals were placed in a sterilized polycarbonate cage with a sterile towel bed for anesthesia recovery. These cages were placed over a circulating warm water bath to provide supplemental heat during the recovery process. After several hours of observation, they were returned to single housing on irradiated bedding in sanitized cages. Buprenorphine was administered twice daily for two days and on the morning of the third day. Enrofloxacin was administered on the evening of surgery and the morning of post-operative day 1. Sutures were removed at approximately 7 days post-surgery, and rats were then pair housed for the study duration.

The animals on study were observed daily. Post-operative radiographs were taken 1) either immediately after surgery or at approximately 1 week post-surgery, 2) at approximately three weeks post-surgery and 3) at sacrifice (approximately 6 weeks post-surgery). All animal radiographs were dorso-ventral views centered on the lower lumbar spine.

Euthanasia was performed approximately 6 weeks post-operatively. Animals were weighed, euthanized in a $CO_2$ chamber and radiographed. The necropsy consisted of explanting the lumbar spine from T13 to approximately S1 or S2. A rib was left on T13 to aid the histo-technician with site orientation. Excessive soft tissue was removed and the operative site identified. A piece of braided suture was placed over the operative site to aid the histo-technician with site identification. The operative segment was manually palpated for motion. After the site was palpated, the spine was placed in 10% neutral buffered formalin. Fresh formalin was exchanged 3-4 days after the necropsies were completed and the samples shipped for histopathology processing and interpretation.

The formalin fixed lumbar spines were processed (Leica TP1050 tissue processor), embedded in paraffin, sectioned, mounted on slides and slides were stained with hematoxylin and eosin (H&E) in an automated stainer (Leica Autostainer XL) using standard histology methodology. H&E stained slides were examined by a veterinary pathologist. Coronal sections of the spines were taken to include the T4 and T5 (T=transverse processes), and the L4 and L5 (L=lumbar) vertebra. Specimens were evaluated for inflammatory response, which was present in all groups, and was minimal to mild in most sites. Specimens were also evaluated for the presence of fusion of T4 to T5, the presence of new bone, the presence of original DBM, and the presence of carrier. The results are shown in Tables 1 (Putty test subjects), 2 (Paste test subjects) and 3 (Shams), in which T=Transverse process, R=Right, L=Left, DBM=Demineralized bone matrix, P=Present, AND A=Absent. Fusion was defined as bridging bone, with or without cartilage, between the transverse processes T4 and T5.

TABLE 1

(Putty of Example 1)

| | Animal #: | | | | | |
|---|---|---|---|---|---|---|
| | 1 | 2 | 3 | 4 | 5 | 6 |
| Group | Putty | Putty | Putty | Putty | Putty | Putty |
| New Bone (R) | P | P | P | P | P | P |
| New Bone (L) | P | P | P | P | P | P |
| Fusion of T4 to T5 (R) | P | P | P | P | P | P |
| Fusion of T4 to T5 (L) | P | P | P | P | P | P |
| Original DBM | P | P | P | P | P | P |
| Carrier | A | A | A | A | A | A |

TABLE 2

(Paste of Example 2)

| | Animal #: | | | | | |
|---|---|---|---|---|---|---|
| | 1 | 2 | 3 | 4 | 5 | 6 |
| Group | Paste | Paste | Paste | Paste | Paste | Paste |
| New Bone (R) | P | P | P | P | P | P |
| New Bone (L) | P | P | P | P | P | P |
| Fusion of T4 to T5 (R) | P | P | A | A | A | P |
| Fusion of T4 to T5 (L) | A | A | P | P | P | A |
| Original DBM | P | P | P | P | P | P |
| Carrier | A | A | A | A | A | A |

TABLE 3

(Sham)

| | Animal #: | | | | | |
|---|---|---|---|---|---|---|
| | 1 | 2 | 3 | 4 | 5 | 6 |
| Group | Paste | Paste | Paste | Paste | Paste | Paste |
| New Bone (R) | A | A | A | A | A | A |
| New Bone (L) | A | A | A | A | A | A |
| Fusion of T4 to T5 (R) | A | A | A | A | A | A |
| Fusion of T4 to T5 (L) | A | A | A | A | A | A |
| Original DBM | A | A | A | A | A | A |
| Carrier | A | A | A | A | A | A |

As can be seen, bilateral new bone was observed in all six animals from in each of the paste and putty groups. Either unilateral or bilateral fusion of T4 to T5 was observed in all six animals from the putty group. Unilateral fusion only (of T4 to T5) was observed in five of six animals in the paste group. It should be noted that while histology provides an accurate means of evaluating bone formation, it is possible to miss bridging bone that might cross out of the plane of section under evaluation.

The spine explants described in the experimental above were also evaluated by manual palpation after harvest. The results are set forth in Table 4 below.

TABLE 4

| | Fusion by Manual Palpation | | | | | | |
|---|---|---|---|---|---|---|---|
| Implant | Rat 1 | Rat 2 | Rat 3 | Rat 4 | Rat 5 | Rat 6 | Fusion |
| Example 1 Putty | A | A | A | A | A | A | 100% |
| Example 2 Putty | A | A | A | A | A | A | 100% |
| Surgical Sham | A | A | A | A | A | A | 0% |

The results demonstrate that the inventive putty and paste formulations successfully achieved fusion in the athymic rat model as assessed by manual palpation.

Example 4

Evaluation of Osteoinductivity

The athymic rat is a widely accepted animal model for testing for osteoinductive activity in DBM products. This model was used to evaluate the inductivity putty formulations prepared as in Example 1 and paste formulations prepared as in Example 2.

The rats in the study were screened for general health before enrollment. The rats were anesthetized with isoflurane throughout the surgical procedure to maintain the proper anesthetic level. Implants were placed singularly in the muscle pouch of each hind limb through a 0.5 cm incision. Implants were placed near the femur to allow for blood supply but not adjacent to the bone. For the putty and paste implants, 0.1 cc of material was used per site. Incisions were closed with suture.

At 28 days post-operative, the rats were sacrificed via carbon dioxide inhalation. The musculature wherein the sample was placed was palpated to locate the implant and discern any tangible signs of calcification. All implants were harvested, preserving record of location. Explants were placed in labeled histology cassettes in 10% neutral buffered formalin.

Samples were decalcified, embedded in paraffin, sectioned & stained. Three sections per implant were taken at 100 μm intervals and stained with H&E. Samples were scored semi-quantitatively according to the table below. A score of one or greater is indicative of a pass, while a score of zero is a fail for the sample. Scores are averaged to determine if the group is a pass or fail. The scoring key was as follows:

| Semi-Quantitative Histologic Scoring | |
|---|---|
| Score | Histologic Appearance |
| 0 | No new bone formation |
| 1 | 1-25% of section area is new bone and/or cartilage formation |
| 2 | 25-50% of section area is new bone and/or cartilage formation |
| 3 | 50-75% of section area is new bone and/or cartilage formation |
| 4 | 75-100% of section area is new bone and/or cartilage formation |

The results are set forth in Table 5 below.

TABLE 5

| | Implant Scores | | | | |
|---|---|---|---|---|---|
| Implant Material | Implant 1 | Implant 2 | Implant 3 | Implant 4 | Average |
| Example 1 Putty | Fail | Pass | Pass | Pass | Pass |
| Example 2 Paste | Fail | Pass | Pass | Pass | Pass |

Thus, the inventive putty and paste formulations were shown to be osteoinductive.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected. In addition, all publications cited herein are hereby incorporated by reference in their entirety.

What is claimed is:

1. A method of treating a bone condition, the method comprising: providing a demineralized bone matrix (DBM) composition, comprising bioresorbable solids admixed with a liquid carrier to form a malleable implant composition, said bioresorbable solids present at a level of about 0.1 grams per cubic centimeter to about 0.7 grams per cubic centimeter of said composition, wherein said bioresorbable solids comprise a particulate solid collagen material and a particulate solid DBM material, said particulate solid collagen material present in a weight ratio no less than 1:12 and no greater than 1:2 relative to said particulate solid DBM material and said liquid carrier comprises an aqueous gel of alginate, wherein said aqueous gel of alginate is present at a level of about 0.01 grams per cubic centimeter to about 0.1 grams per cubic centimeter of said composition; applying a divalent cation to the DBM composition; and administering the composition to a location in a subject where bone growth is desired.

2. The method according to claim 1, wherein applying a divalent cation comprises applying calcium chloride.

3. The method according to claim 1, wherein applying a divalent cation comprises applying calcium or strontium.

4. The method according to claim 3, comprising applying calcium.

5. The method according to claim 1, further comprising applying a BMP protein to the DBM composition.

6. The method according to claim 5, wherein the BMP protein is selected from the group consisting of rhBMP-2, rhBMP-3, rhBMP4, rhBMP5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12 and rhGDF-14.

7. The method according to claim 6, wherein said BMP protein is rhBMP-2.

8. The method according to claim 7, wherein applying a divalent cation comprises applying calcium chloride.

9. The method according to claim 5, further comprising applying the divalent cation to the BMP protein and DBM composition.

10. The method according to claim 9, further comprising applying the divalent cation to the BMP protein and DBM composition following administering the composition to the subject.

11. The method according to claim 9, further comprising applying the divalent cation to the BMP protein and DBM composition prior to administering the composition to the subject.

12. The method according to claim 5, wherein applying a divalent cation comprises applying calcium or strontium.

13. The method according to claim 9, wherein applying a divalent cation comprises applying calcium chloride.

14. The method according to claim 10, wherein applying a divalent cation comprises applying calcium chloride.

15. The method according to claim 11, wherein applying a divalent cation comprises applying calcium chloride.

* * * * *